United States Patent
Frater et al.

(10) Patent No.: US 6,255,276 B1
(45) Date of Patent: Jul. 3, 2001

(54) ODORANT COMPOSITIONS CONTAINING MACROCYCLES AND PROCESSES FOR MANUFACTURING THE SAME

(75) Inventors: Georg Frater, Winterthur; Daniel Helmlinger, Dübendorf; Urs Müller, Zürich, all of (CH)

(73) Assignee: Givauden Roure (International) S.A., Vernier (CH)

( * ) Notice: Subject to any disclaimer, the term of this patent is extended or adjusted under 35 U.S.C. 154(b) by 0 days.

(21) Appl. No.: 09/504,471

(22) Filed: Feb. 16, 2000

Related U.S. Application Data

(63) Continuation of application No. 09/162,175, filed on Sep. 28, 1998, now abandoned.

(30) Foreign Application Priority Data

Oct. 9, 1997 (CH) .................................................. 2362/97

(51) Int. Cl.⁷ ...................................................... A61K 7/46
(52) U.S. Cl. .......................... 512/11; 549/266; 549/273; 549/294
(58) Field of Search ............................... 512/11; 549/266, 549/273, 294

(56) References Cited

U.S. PATENT DOCUMENTS

| | | | |
|---|---|---|---|
| 4,064,144 | 12/1977 | Tseng | 528/388 |
| 4,541,950 | 9/1985 | Van Loveren et al. | 512/8 |
| 5,266,559 | 11/1993 | Frankhauser et al. | 512/11 |

FOREIGN PATENT DOCUMENTS

| | | |
|---|---|---|
| 344 712 | of 1960 | (CH) . |
| 424 787 | of 1990 | (EP) . |
| 818 452 | of 1998 | (EP) . |
| 490 044 | of 1938 | (GB) . |
| WO 97/32948 | of 1997 | (WO) . |

OTHER PUBLICATIONS

Buchi, G. *Helvetica Chimica Acta.*, 62(8):2661–72 (1979).
Nicolaou, K.C., et al. *J. Org. Chem.*, 44(22):4011–13 (1979).
Galli, C., et al. *J. Org. Chem.*, v.44(8):1258–61 (1979).
Collaud, C. *Helvetica Chimica Acta.*, 25:965–75 (1942).
Furstner, A., et al. *J. Org. Chem.*, 61:3942–43 (1996).
Hanack, M. *Houben–Weyl.*, V/1b, 105–9 (1972).
Mookherjee, B.D., et al. *J. Org. Chem.*, 37(24): 3846–48 (1972).
Maurer, B., et al., *Helvetica Chimica Acta.*, 60(4):1155–60 (1977).
*Parfums, Cosmetiques, Actualiees.*, No. 128, avril/mai 63, (1996).
Chemical Abstracts, vol. 96, No. 27 (1982).

*Primary Examiner*—Amelia Owens
(74) *Attorney, Agent, or Firm*—Mark E. Waddell; Stephen M. Haracz; Bryan Cave LLP

(57) ABSTRACT

The invention is concerned with odorant compositions which contain macrocycles, namely 15- to 17-membered compounds of the formula:

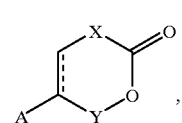

Figure 1:
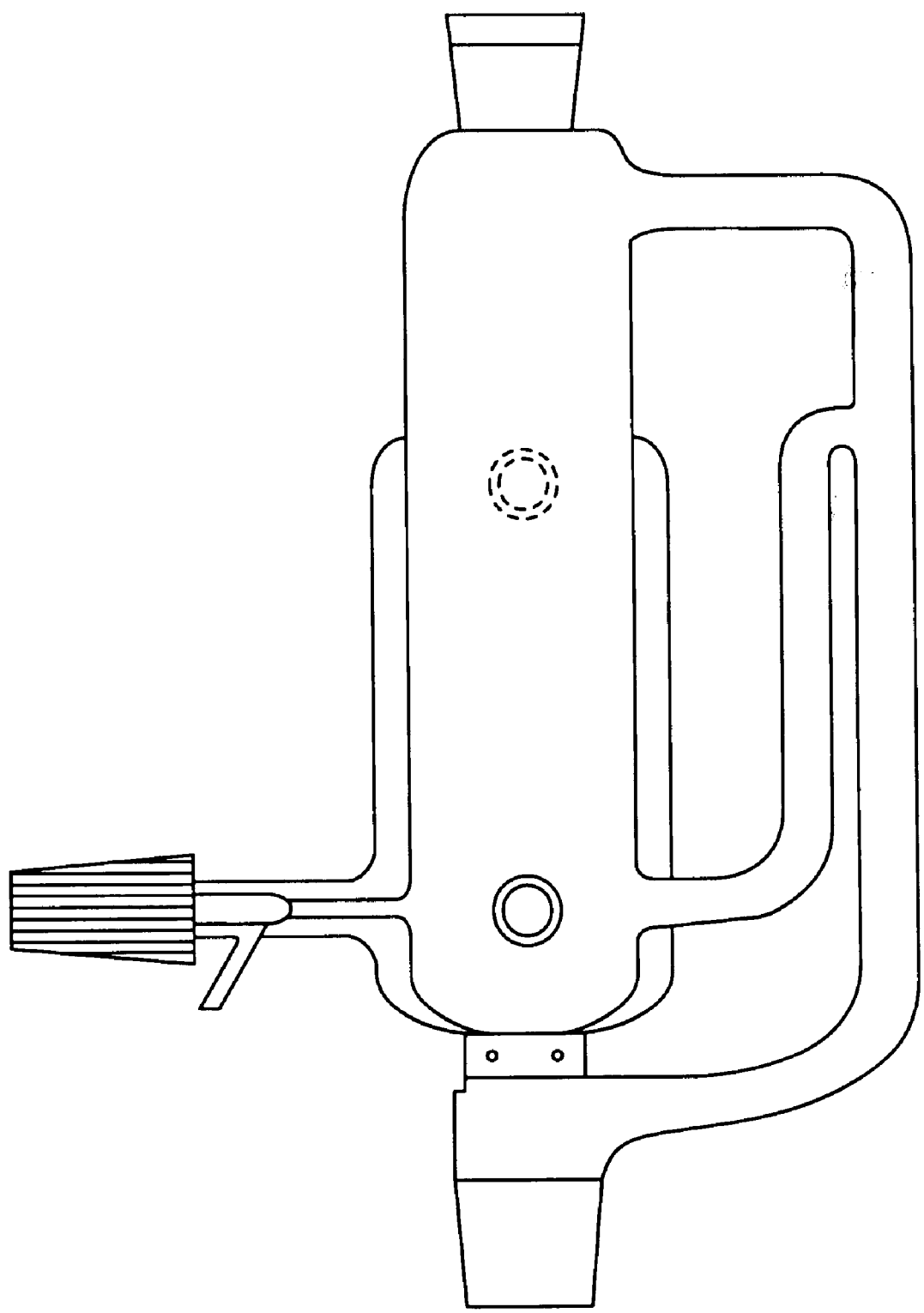

I wherein the dotted line signifies an optional additional bond, X and Y stand for methylene or $C_{2-12}$-polymethylene, optionally substituted with an additional methyl group, and A signifies hydrogen or methyl in the case of the unsaturated compounds and methyl in the case of the saturated compounds, with the proviso that the unsaturated compounds are present to more than 80% in the cis form when A signifies hydrogen and are present to more than 50% in the cis form when A signifies methyl, with the exception of Z-oxacyclopentadec-6-en-2-one (15-membered ring), Z-oxacycloheptadec-8-en-2-one (17-membered ring), and Z-oxacycloheptadec-11-en-2-one (17-membered ring), a process for the manufacture of the compounds of formula I and the use of the compounds of formula I as odorants.

20 Claims, 1 Drawing Sheet

ODORANT COMPOSITIONS CONTAINING MACROCYCLES AND PROCESSES FOR MANUFACTURING THE SAME

This application is a continuation of Ser. No. 09/162,175 filed Sep. 28, 1998 now abandoned.

BACKGROUND OF THE INVENTION

The present invention provides odorant compositions containing macrocycles, namely 15 to 17-membered compounds of the formula

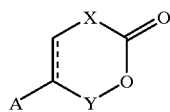

wherein the dotted line signifies an optional additional bond; one or both of X and Y are methylene or $C_{2-12}$-polymethylene, optionally substituted with an additional methyl group; and A is hydrogen or methyl when the compounds are unsaturated and methyl when the compounds are saturated providing that the unsaturated compounds are in at least 80% cis form when A is hydrogen and are in at least 50% cis form when A is methyl with the exception of Z-oxacyclopentadec-6-en-2-one (15-membered ring), Z-oxacydoheptadec-8-en-2-one (17-membered ring) and Z-oxacycloheptadec-11-en-2-one (17-membered ring). The present invention also provides a process for the manufacture of the compounds of formula I.

The compounds I or the defined mixtures I with the substituents previously defined for formula I are novel with the exception of Z-oxacyclopentadec-3-(or 6-or 13-)en-2-one, Z-oxacyclohexadec-3-(or 6-, 11-, 12- or 13)en-2-one and Z-oxacycloheptadec-8-(or 10-, 11-, 12-, 13- or 15-)en-2-one.

The compounds I thus embrace oxacyclopenta(or -hexa or -hepta)decen-2-ones and the respective corresponding decan-2-ones.

Formula I is intended to include all possible isomers. Thus, in the case of saturated and unsaturated compounds the racemates and the optically active compounds, that is to say the R- and S-forms, are included. In the case of the unsaturated compounds the cis/trans ratio is that according to the above definition. Further, diastereoisomeric forms are also possible with regard to multi-methyl substitutions.

Some derivatives of decan-2-ones and/or synthesis thereof have been described in articles, United States Patents and European Patents. Several of these references, as well as how the compounds described therein differ from the present invention, are discussed below.

In 1927 ambrettolide (Z-oxacycloheptadec-8-en-2-one) was isolated from ambrette seed oil (musk seed oil) (Ber. 60,902,(1927). In 1977 Z-oxacyclopentadec-6-en-2-one was isolated from the same oil (B. Maurer, A. Grieder, Helv. Chim. Acta, 60, 1155, (1977). The synthesis of E-oxacydoheptadec-10-en-2-one is the subject of U.S. Pat. No. 4,064,144.

The synthesis of a mixture of oxacydoheptadec-8-en-2-one, oxacyclo-heptadec-9-en-2-one, oxacycloheptadec-10-en-2-one and oxacycloheptadec-11-en-2-one, with the third compound being present in amounts up to 80% in the aforementioned mixture has been described in the literature. B. D. Mookherjee, R. W. Trenlde, R. R. Patel, J. Org. Chem. 37, 24, 3846, (1972). Although the stereochemistry of these compounds was not indicated, since the aforementioned synthesis is a pyrolysis of an ester, a selective formation of a cis-olefin would not be expected (see, Houben-Weyl, volume V/1b, 105, 1972).

A mixture of mainly E-oxacyclohexadec-12-en-2-one and E-oxacyclohexadec-13-en-2-one, with the Z-isomers being present only in a small percentage is the subject matter of European Patent No.0,424,787.

The use of oxacyclohexadec-11-en-2-one is the subject of U.S. Pat. No. 4,541,950. Although the use of the aforementioned compound is the subject of a U.S. patent, the cis/trans ratio of the product obtained is not given. However, since the product was obtained by metathesis, it is doubtful whether the trans content is higher than the cis content. (See, A. F ürstner, K. Langemann, J. Org. Chem. 61, 3942, 1996.)

The French company Mane et Fils in F-06620 Bar s/Loup sells a compound under the name cis-iso-ambrettolide which is Z-oxacycloheptadec-11-en-2-one (Parfums, Cosmétiques, Actualiées, No 128, avril/mai 63, 1996).

C. Collaud (Helv. Chim. Acta 25, 965, 1942) describes the production of a mixture of oxacycloheptadec-6-en-2-one and oxacydoheptadec-7-en-2-one without describing the stereochemistry of the products. However, since the aforementioned synthesis is a pyrolysis of an ester, a selective formation of a cis-olefin is not expected.

Unlike the aforementioned compounds, compounds of formula I have extremely low threshold values and very good adhesion properties. All compounds of formula I have intensive musk notes, which are often accompanied by powdery, fruity, flowery side-notes. In addition, compounds of formula I also have amber-like, earthy notes similar to the scent of ambrette seeds. Z-13-methyl-oxacyclopentadec-10-en-2-one in particular has an especially fine perfumistic effect with a dominant musk note. This musk note is rounded off by a powdery, fruity component.

SUMMARY OF THE INVENTION

The present invention provides odorant compositions having extremely low threshold values and very good adhesion properties. These compositions also have intensive musk notes, which are often accompanied by powdery, fruity, amber-like, earthy notes and flowery side-notes. The compositions also have amber-like, earthy notes similar to the scent associated with ambrette seeds.

The odorant compositions containing macrocycles, namely 15 to 17-membered compounds have the formula:

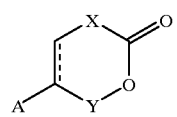

wherein the dotted line signifies an optional additional bond; X and Y is methylene or $C_{2-12}$-polymethylene, optionally substituted with an additional methyl group; and A is hydrogen or methyl when the compounds are unsaturated and methyl when the compounds are saturated providing that the unsaturated compounds are present in at least 80% cis form when A is hydrogen and are present in at least 50% cis form when A is methyl with the exception of Z-oxacydopentadec-6-en-2-one (15-membered ring), Z-oxacycloheptadec-8-en-2-one (17-membered ring) and Z-oxacycloheptadec-11-en2-one (17-membered ring). The present invention also provides a process for the manufacture of the compounds of formula I.

Another embodiment of the present invention is an odorant composition, which contains at least one 15–17 membered lactone compound of the formula:

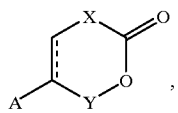

wherein the dotted line signifies an optional additional bond but which in case of a 16-membered lactone compound is not placed at position 11, 12 or 13; one or both of X and Y is methylene or $C_{2-12}$-polymethylene, optionally substituted with an additional methyl group with the proviso that the sum of carbon atoms of X and Y is 11, 12 or 13, and A is hydrogen or methyl when the compound is unsaturated and methyl when the compound is saturated providing that the unsaturated compounds are in at least 80% of cis form when A is hydrogen and are in at least 50% of cis form when A is methyl, with the exception of Z-oxacyclopentadec-6-en-2-one, Z-oxacycloheptadec-8-en-2-one and Z-oxacycloheptadec-11-en-2-one.

The odorant composition set forth above may contain at least one compound selected from the following group: Z-oxacycloheptadec-12-en-2-one, Z-oxacylohexadec-5-en-2-one, Z-oxacycloheptadec-7-en-2-one, Z-oxacycloheptadec-13-en-2-one, Z-oxacycloheptadec-10-en-2-one, Z-oxacycloheptadec-8-en-2-one, and Z-4-methyl-oxacyclohexadec-6-en-2-one.

The odorant composition set forth above may also contain at least one compound selected from the following group: oxacycloheptadec-12-en-2-one, oxacycloheptadec-9-en-2-one, oxacycloheptadec-7-en-2-one, oxacycloheptadec-13-en-2-one, oxacycloheptadec-10-en-2-one, oxacycloheptadec-14-en-2-one, 15-methyl-oxacycloheptadec-12-en-2-one, 13-methyl-oxacyclopentadec-10-en-2-one, oxacyclohexadec-5-en-2-one, 10-methyl-oxacyclopentadec-9-en-2-one, 10-methyl-oxacyclopentadecan-2-one, 8-methyl-oxacyclopentadec-7-en-2-one, 8-methyl-oxacyclopentadecan-2-one, 9,13-dimethyl-oxacyclopentadec-8-en-2-one, 7-methyl-oxacyclohexadec-6-en-2-one, 4-methyl-oxacyclohexadecan-2-one, 7-methyl-oxacyclohexadecan-2-one, and 8,15-dimethyl-oxacyclopentadec-7-en-2-one.

The odorant composition is preferably 13-methyl-oxacyclopentadec-10-en-2-one, 13-methyl-oxacyclopentadec-10-en-2-one having the Z-(13S)-configuration, or 13-methyl-oxacyclopentadec-10-en-2-one having the Z-(13R)-configuration.

Another embodiment of the present invention provides compounds of the formula:

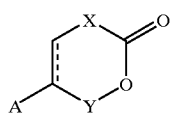

wherein the dotted line signifies an optional additional bond but which in case of a 16-membered lactone compound is not placed at position 11, 12 or 13; one or both of X and Y is methlylene or $C_{2-12}$-polymethylene, optionally substituted with an additional methyl group with the proviso that the sum of carbon atoms of X and Y is 11, 12 or 13, and A is hydrogen or methyl when the compound is unsaturated and methyl when the compound is saturated providing that the unsaturated compounds are in at least 80% of cis form when A is hydrogen and are in at least 50% of cis form when A is methyl, with the exception of Z-oxacyclopentadec-3-en-2-one, Z-oxacyclopentadec-6-en-2-one, Z-oxacyclopentadec-13-en-2-one, Z-oxacyclohexadec-3-en-2-one, Z-oxacyclohexadec-6-en-2-one, Z-oxacycloheptadec-8-en-2-one, Z-oxacycloheptadec-10-en-2-one, Z-oxacycloheptadec-11-en-2-one, Z-oxacycloheptadec-12-en-2-one, Z-oxacycloheptadec-13-en-2-one, and Z-oxacycloheptadec-15-en-2-one.

Thus, a compound as set forth above may be selected from the following group: Z-oxacylohexadec-5-en-2-one, Z-oxacycloheptadec-7-en-2-one, and Z-4-methyloxacyclohexadecan-2-one.

A preferred compound according to the formula set forth above is 13-methyl-oxacyclopentadec-10-en-2-one, Z-(13R)-methyl-oxacyclopentadec-10-en-2-one, or Z-(13S)-methyl-oxacyclopentadec-10-en-2-one.

Formula I of the present invention also includes the following compounds: oxacyclohexadec-5-en-2-one, 10-methyl-oxacyclopentadec-9-en-2-one, 10-methyl-oxacyclopentadecan-2-one, 8-methyl-oxacyclopentadec-7-en-2-one, 8-methyl-oxacyclopentadecan-2-one, 15-methyl-oxacycloheptadec-12-en-2-one, 9,13-dimethyl-oxacyclopentadec-8-en-2-one, 7-methyl-oxacyclohexadec-6-en-2-one, 7-methyl-oxacyclohexadecan-2-one, 4-methyl-oxacyclohexadecan-2-one, 8,15-dimethyloxacyclopentadec-7-en-2-one.

The present invention also includes a process for the manufacture of the compounds of formula I. This process includes lactonizing a compound of the formula

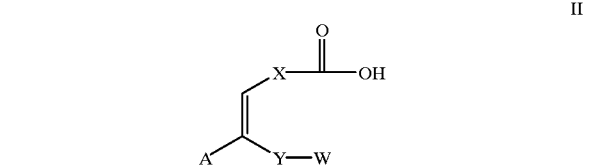

wherein A is hydrogen or methyl when the compound is unsaturated and methyl when the compound is saturated providing that the unsaturated compounds are in at least 80% cis form when A is hydrogen and are in at least 50% cis form when A is methyl with the exception of Z-oxacyclopentadec-6-en-2-one, Z-oxacycloheptadec-8-en-2-one, and Z-oxacycloheptadec-11-en-2-one; X and Y is methylene or $C_{2-12}$-polymethylene, optionally X and Y substituted with an additional methyl group; and W is OH, O-alkanoyl or a leaving group.

DETAILED DESCRIPTION OF THE INVENTION

As stated above, the odorant compositions of the present invention have extremely low threshold values and good adhesion properties. One compound in particular, Z-13-methyl-oxacyclopentadec-10-en-zone, has a very low threshold value of 0.578 ng/l. The GC threshold value is 0.1 ng/l. This gives an "Odor value" of 18038 [see N. Neuner-Jehle, F. Etzweiler, in Perfumes: Art Science and Technology, Edited by P. M. Müller, D. Lamparsky] which is higher than any "Odor value" currently known for a macrocydic musk. For example, Musk R1 (1,7-dioxa-cycloheptadecan-8-one) has a threshold value of 0.33 ng/l; a vapour pressure of 3.24 μg/l and an "Odor value" of 3074. Thibetolide has a threshold value of 2.16 ng/l, a vapour pressure of 6.64 µg/l and an "Odor value" of 3074. All other macrocyclic musk odorants have even lower values. In addition, Z-13-Methyl-oxacyclopentadec-10-en-2-one has a powdery, musk-like, lactone-like, fruity Odor.

Other preferred compounds used in accordance with the present invention are described below.

Z-Oxacycloheptadec-12-en-2-one, has a strong, thibetolide-like Odor similar to ambrette seeds.

Another odorant is—Z-oxacyclohexadec-5-en-2-one, which has a musk-like, powdery, lactonic Odor.

Still another odorant is—Z-oxacyclohepadec-9-en-2-one, which has never been produced to the purity level achieved by the present invention. Nor has the spectral data and olfactory properties of this compound ever been obtained. This compound has a strong nitromusk note, with a lactonic, woody, animalic impact.

Still yet another odorant is—Z-oxacycloheptadec-10-en-2-one which has a musk-like Odor similar to both ambrettolide and ambrette seeds. Additional odors of this compound include powdery, fruity and green notes.

Still yet another odorant is—10-methyl-oxacyclopentadecan-2-one which has a nitromusk-like, powdery, lactonic, woody, earthy Odor.

Still yet another odorant is—8-methyl-oxacyclopentadecan-2-one which has a nitromusk-like, powdery, amber-like, fruity Odor.

Still yet another odorant is—9,13-dimethyloxacyclopentadecan-2-one which has a musk-like, fruity, powdery, flowery, lactone-like Odor.

Still yet another odorant is—oxacycloheptadec-7-en-2-one which has fruity, musk-like, flowery, Odor similar to ambrette seeds.

Still yet another odorant is—Z-oxacydoheptadec-13-en-2-one which is very desirable having a musk ketone-like, powdery, lactonic, flowery Odor.

Still yet another odorant is—7-methyl-oxacyclohexadecan-2-one which has a musk-like, flowery, fruity, powdery, lactone-like Odor.

Still yet another odorant is—8,15-dimethyl-oxacyclopent-7-en-2-one which has a nitromusk, powdery, animalic odor.

Still yet another odorant is—15-methyl-oxacyclohepadec-12-en-2-one which has a distinguishable musk-like, woody, animalic, sweet earthy, fruity odor.

The macrocycles of formula I including the odorants listed above, can be used generally in the same manner as musk odorants known in the art. Thus, the compounds of the present invention harmonize with a large number of natural and synthetic products frequently used in odorant compositions. In particular, the base note produces interesting effects when combined with woody and amber accords, patchouli oil as well as cedarwood and sandalwood odorants. Flowery middle notes confer elegance and radiance to the compounds of the present invention. Some examples of classes of substances which harmonize well include: natural products, such as tree moss absolute, geranium oil, jasmin absolute, patchouli oil, rose oil, sandalwood oil, vetiver oil and ylang-ylang oil, etc. Alcohols, such as citronellol, Ebanol®, geraniol, linalool, phenylethyl alcohol and Sandalore®, etc. Adehydes and ketones, such as Florozone® (3-(4-ethylphenyl)-2,2-dimethyl-propional), hydroxycitronellal, Iso-E-Super® (1,2,3,4,5,6,7,8-octahydro-2,3,8,8-tetramethyl-2-octanaphthalene), Isoraldein®, maltol, methyl edryl ketone, methylionone and vanillin, etc. Ethers and acetals, such as ambrox, geranyl methyl ether, rose oxide and Spirambrene® (2',2',3,7,7-pentamethyl-spiro[bicyclo [4.1.0]heptane-2,5'-[1,3]dioxan]), etc; and esters and lactones, such as Berryflor®, γ ecalactone and γ-undecalactone, etc.

The versatility of the compounds of the present invention permit a wide use of the compounds, not only in sweet oriental creations, but also in "fougére", "chypre" and "floral" olfactory combinations. By virtue of their low threshold values and the good adhesion properties, compositions for cosmetic products, washing agents and similar mass produced products are also contemplated in addition to luxury perfumes.

The compounds of formula I can be used in compositions having a wide variety of concentrations, for example, from about 0.1 wt. % (detergents) to about 40 wt. % (alcoholic solutions). These values are not, however, limiting values, since the experienced perfimer can also produce effects with even lower concentrations or can synthesize novel complexes with even higher amounts. The preferred concentrations range between about 3% and about 20%. The compositions manufactured with compounds of formula I can be used for all kinds of perfumistic consumer goods such as, eaux de Cologne, toilet water, extracts, lotions, creams, shampoos, soaps, salves, powders, deodorants, detergents, etc.

Accordingly, the compounds of formula I can be used for the production of compositions containing a wide range of known odorants or odorant mixtures. In the production of such compositions the odorants or odorant mixture set forth above can be use in a manner known to the perfumer. For example, as described in W. A. Poucher, Perfumes, Cosmetics, Soaps, 2nd vol., 7th edition, Chapman and Hall, London 1974.

The process for the manufacture of the compounds of formula I or mixtures thereof comprises lactonizing a compound of the formula

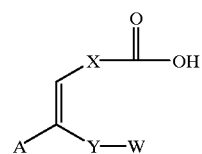

II wherein A is hydrogen or methyl when the compound is unsaturated and methyl when the compound is saturated providing that the unsaturated compounds are in at least 80% cis form when A is hydrogen and are in at least 50% cis form when A is methyl with the exception of Z-oxacyclopentadec-6-en-2-one (15-membered ring), Z-oxacycloheptadec-8-en-2-one (17-membered ring) and Z-oxacycloheptadec-11-en-2-one (17-membered ring); X and Y is methylene or $C_{2-12}$-polymethylene, optionally substituted with an additional methyl group and W represents OH, alkanoate, for example acetate, or a leaving group, such as mesylate, tosylate, I, Br, Cl etc., in a manner known per se, namely at elevated temperature and under basic conditions, and, if desired, hydrogenating a resulting unsaturated compound of formula I.

The compounds of formula II can be obtained by subjecting a compound of the formula

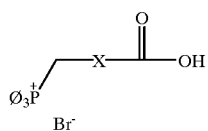

to a Wittig reaction with a compound of the formula

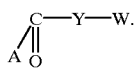

The lactonization of a compound of formula II to a compound of formula I can be effected, for example, according to the method of Collaud (BP No. 490 044, Jan. 4, 1937, C. Collaud, Helv. Chim. Acta, 965, 1942).

Here, the preparation of an ω-hydroxycarboxylic acid 2,3-dihydroxy-propyl ester is effected first by treatment of the sodium salt of the corresponding ω-hydroxycarboxylic acid of formula II with chloropropane-1,2-diol, followed by an internal trans-esterification in the presence of a methanolate, particularly sodium methanolate. The resulting monomer is distilled from the reaction mixture in the presence of a high-boiling solvent or entraining agent, for example glycerol.

An alternate way for the lactonization of a compound of formula II to a compound of formula I to occur is described, for example, in Patent CH 344 712. The ω-hydroxycarboxylic acid is heated at a high temperature in the presence of a base (KOH, NaOH, etc.) and glycerol, with a polyester being obtained. Subsequently, an internal trans-esterification is effected in the presence of sodium methylate. The resulting monomer is distilled from the reactor in a high-boiling solvent, for example glycerol.

When W stands for I, Br or Cl, the lactonization of a compound of formula II to formula I can also be achieved according to the method of Mandolini et al. (G. Galli, G. Giannelli, G. Illuminati, L. Mandolini, J. Org. Chem., Vol. 44, No. 8, 1258, 1979). Here, the ω-bromoalkanoate of formula II is added dropwise to a well-stirred suspension of potassium carbonate in dimethyl sulphoxide.

The use of these known methods described above is, however, not suitable the manufacture of odorants, since sulphur notes are difficult to remove from the final product. It has now been found that dimethyl sulphoxide can be replaced by a sulphur-free solvent, in particular N-methylpyrrolidone, and that an olfactorily perfect product can be obtained in this manner.

The hydrogenation of an unsaturated compound of formula I can be effected according to methods well known in the art, namely catalytically. Suitable catalysts include Pd-on-carbon or on potassium carbonate, Pt or Raney-nickel as well as other catalysts well known in the art used in hydrogeneration of unsaturated compounds. Hydrogeneration is conveniently carried out in a solvent such as an alkanol, for example methanol, ethanol etc., in ethyl acetate or acetic acid etc. The suitable temperature range extends from about room temperature to about 100° C. The hydrogenation can be carried out under normal pressure or under elevated pressure. Thus, for example, a pressure up to about 60 atm. or even higher is within the scope of this invention.

The preparation of the compounds of formula II can be achieved according to methods per se well known in the art for Wittig reaction. Accordingly, a phosphonium salt of formula III is conveniently treated firstly with (about 2 equivalents) of a strong base to give an ylid. Potassium t-butylate, potassium t-amylate, methyllithium, butyllithium, phenyllithium, potassium hydride, sodium hydride, hexamethyldisilazane (as the potassium or sodium salt), lithium diisopropylamide etc. can be used as bases. An aprotic solvent such as diethyl ether, tetrahydrofuran, benzene, toluene, hexane, dimethylformamide, HMPA (hexamethal-phosphoric acid triamide) etc. is preferably used as the medium for the further reaction with a compound of formula IV. The temperatures are not critical, and the convenient temperature range can be broad (about −78 to about 100° C.).

The Wittig reaction has been used sporadically for the synthesis of precursors of macrocyclic compounds (Nicolaou et al., J. Org. Chem. 44,4011, 1979). Büchi and Wuest (Helv. Chim. Acta, 62, 2661, 1979) have used the Horner-Emmons condensation including a Wittig reaction for the synthesis of the cyclic $C_{15}$-ketones exaltone and muscone. However, using the Wittig reaction for the synthesis of macrocyclic lactones, in addition to various ring sizes having double bonds in various positions, has been unknown until now.

The process in accordance with the invention permits for the first time the manufacture of substituted or unsubstituted macrocyclic lactones with ring sizes of 15, 16 and 17 having an optional double bond, and which are mainly in the cis form.

EXAMPLES

The present invention is described further in the following examples which are presented solely for the non-limiting purpose of further illustrating the invention.

Example 1

100 g (0.846 mol), of 3-methyl-1,5-pentanediol, 108 ml of ethyl acetate and 21 g of Amberlyst® 15 dissolved in 420 ml of toluene were heated at 94° C. to reflux temperature for 3 hours. Then, the mixture was cooled, filtered over Celite and concentrated on a rotary evaporator. 104.5 g of crude product comprising, as a mixture, 3-methyl-1,5-pentanediol (25%), 3-methyl-1,5-pentanediol monoacetate (50%) and 3-methyl-1,5-pentanediol diacetate (25%).

Example 2

189 g of crude product (from the preceding Example) and 9 g (76 mol) of potassium bromide were placed in 377 ml of methylene chloride and treated at −100° C. with 1.18 g (7.55 mmol) of 2,6,6-tetramethylpiperidin-1-oxyl radical. 780 ml of 12–15 percent hypochlorite solution (adjusted to pH 9 with 19.gl $NaHCO_3$) were added dropwise at 0–5° C. within 50 minutes. After 40 minutes the temperature rose to 18° C. in spite of cooling. The mixture was stirred at 2–8° C. for 1 hour. Subsequently, a further 195 ml of 12–15 percent hypochlorite solution (adjusted to pH 9 with 19 g/l $NaHCO_3$) were added dropwise at 0–5° C. within 15 minutes. The mixture was stirred for 30 minutes, with the temp. rising to 10° C. A further 195 ml of 12–15 percent hypochlorite solution (adjusted to pH 9 with 19 g/l $NaHCO_3$) were added dropwise within 10 minutes, with the temp. rising to 6° C. The mixture was stirred at 0–5° C. for a further 1 hour and 30 minutes. The reaction mixture was poured into water and extracted twice with methylene chloride. The organic phase was washed (peroxide test negative) with 2N HCl+5 g Kl and with water+9 g $Na_2S_2O_3·5H_2O$. Thereafter it was dried over $Na_2SO_4$ and concentrated. 177 g of crude product were obtained. This crude product was distilled and gave 114 g of product (b.p. 75–76° C., 0.2 bar) (content ~70% of 3-methyl-5-oxopentanol acetate according to $^1$H-NMR).

Example 3

156 g (0.312 mol) of (8-carboxyoctyl)-triphenylphosphonium bromide were pulverized and placed in 330 ml of tetrahydrofuran. After stirring for 10 minutes the mixture was cooled to −20° C. and treated rapidly with 69.9 g (0.622 mol) of potassium t-butylate in 90 ml of tetrahydrofuran. The temperature. rose to 6° C. and the reaction mixture became dark red in colour. It was diluted with 50 ml of tetrahydrofuran and stirred at 5–10° C. for 1 hour. Then, it was cooled to −20° C. and treated with 70 g (0.30 ml, 70%) of 3-methyl-5-oxopentanoyl acetate in 50 ml of tetrahydrofuran. The temperature thereby rose to 15° C. The mixture was stirred at −10° C. to −8° C. for 1 hour and thereafter at room temperature for 1 hour. It was warmed to 35° C. and stirred for an additional 30 minutes. The reaction mixture was poured into water, adjusted to pH 12 with 2N NaOH and extracted twice with ether. The organic phase was washed with 2N NaOH and the aqueous phase was acidified with 85 percent ortho-phosphoric acid and extracted twice with ether. The organic phase was washed with saturated sodium chloride solution, dried over sodium sulphate and concentrated. 106 g of crude product were obtained, which was purified by chromatography. The impurities (~36 g) were mainly triphenyl- phosphine oxide. The product consisted of a mixture of 9-Z-14-acetoxy-12-methyltetradec-9-enoic acid and 9-Z-14-hydroxy-12-methyltetradec-9-enoic acid in the ratio 2:1.

Spectra of 9-Z-14-hydroxy-12-methyltetradec-9-enoic acid having the following characteristics: Z/E =94/6;

IR (film): 3336; 3005; 2928; 2855; 1711; 1458; 1246; 1057;

$^1$H-NMR (CDCl$_3$, 200 MHz) 5.4 (2H) m; 3.7 (2H) m; 2.32 (2H) t δ=7 Hz; 0.9 (3H) dδ=6.2; and MS 238 (2); 150 (4); 136 (5); 109 (16); 95 (32); 81 (100); 67 (48); 55 (76); 41 (48).

Example 4

Apparatus:

350 ml 3-necked sulphonation flask, special headpiece reflux condenser, thermostat, 2 cooling traps, HV pump with constantly maintained vacuum.

53.5 g of crude product (~65 percent) from the preceding Example, 230 ml of glycerol and 1 g of potassium hydroxide (85 percent) in 1 ml of water were placed in a 350 ml sulphonation flask having a distillation headpiece. The resulting water, acetic acid and 4–5 ml of glycerol were distilled off in a high vacuum. Thereupon, the distillation headpiece was removed and the flask was fitted with the described special headpiece. This was filled with 150 ml of glycerol. The mixture was left to cool and 1 g of sodium methylate was added. The methanol formed was removed in a vacuum. The mixture was heated to 170–180° C. under reflux (internal initial temperature 155° C.) in a high vacuum. (3–4 mbar) for 18 hours. After this time a 15 mm thick layer of lactone had formed in the special headpiece. It was left to cool. 1 g of sodium methylate was added to the lactone and the methanol formed was distilled off in vacuum. After distillation for 42 hours. the addition was repeated. After a total of 66 hours. at reflux it was left to cool. The content of the headpiece was diluted with water and extracted four times with ether. The organic phase was washed with water, dried over sodium sulphate and concentrated. 28 g of crude product were obtained which was distilled (difflusion pump) over a Widmer column. 20 g (69%) of 13-methyloxacyclopentadec-10-en-2-one were obtained having the following characteristics, Z/E=94/6;

IR (film): 3008; 2927; 2857; 1734; 1459; 1378; 1245; 1180; 1146; 1055;

$^1$H-NMR (CDCl$_3$, 200 MHz) 5.45 (2H) m; 4.2 (2H) m; 0.95 (3H) dδ=6.2 Hz;

$^{13}$C-NMR (CDCl$_3$) 173.9 (s); 131.3 (d); 127.8 (d); 61.9 (t); 36.2 (t); 34.0 (t); 33.9 (t); 31.2 (d); 27.62 (t); 27.60 (t); 27.1 (t); 26.8 (t); 25.6 (t); 24.8 (t) 18.6 (9). MS 238 (2); 196 (2); 150 (5); 136 (5); 123 (5); 109 (14); 95 (30); 81 (100); 67 (49); 55 (53); 41 (48); 27 (15); and a musk-like, fatty, fruity, powdery, lactone-like odor.

Example 5

527 g (1 mol) of 10-carboxydecyltriphenylphosphonium bromide were suspended in 1.4 liter of tetrahydrofuran. 248 g (2.2 mol) of potassium t-butylate dissolved in 1 liter of tetrahydrofuran were added at 0° C. After stirring at 5° C. for 30 minutes 120 g (1.18 mol) of tetrahydropyran-2-ol were added at 0–10° C. The reaction mixture was stirred at room temperature for 90 minutes, poured into water and extracted with t-butyl methyl ether. The aqueous phase was adjusted to pH 2 with 4N sulphuric acid and extracted with t-butyl methyl ether. 274 g of crude product were obtained. For the purification of the aforementioned crude product, 552 g were esterified with 700 ml of methanol and 10 ml of sulphuric acid as the catalyst (3 hours, reflux temperature). After usual work up 620 g of crude ester were obtained which was distilled. As a result, 301 g (53%) of methyl 16-hydroxyhexadec-11-enoate, Z/E=94/6, were obtained.

Example 6

240 g (0.84 mol) of methyl Z-16-hydroxyhexadec-11-enoate and 50 g of potassium hydroxide were dissolved in 500 ml of methanol in a 3 liter flask. The mixture was heated to reflux temperature for 2 hours. Then, the methanol was distilled off and 800 ml of glycerol were added to the residue. 250 ml of glycerol were distilled off (150° C., 3 mmHg). 160 g (1.45 mol) of 3-chloropropane-1,2-diol were added slowly at 150° C. and the mixture was stirred at this temperature for 1 hour. Then, 200 ml of a mixture of 3-chloropropane-1,2-diol and glycerol were distilled off (120–148° C. 3 mmHg, internal temperature 160–170° C.). The mixture was cooled to 60° C. and treated at this temperature with 25 ml of 5.4M ethanolic sodium methanolate solution. The mixture was distilled further (3 mmHg, 180–200° C.) and glycerol was replaced continuously. After 950 ml of a two-phase mixture had been distilled off the residue was extracted with hexane. After distillation there were obtained 167 g (78%) of 12Z-oxacycloheptadec-12-en-2-one, were obtained having the following characteristics: Z/E=91/9;

IR (film) 2928; 2857; 1736; 1461; 1245; 1174;

$^1$H-NMR (CDCl$_3$, 200 MHz) 5.35 (2H) m; 4.1 (2H) tδ=6.5 Hz); 2.32 (2H) t δ=7.5 Hz. $^{13}$C-NMR (CDCl$_3$) 173.35 (s); 130.04 (d); 129.06 (d); 63.83 (t); 34.09 (t); 28.43 (t); 28.27 (t); 28.15 (t); 27.34 (t); 27.10 (t); 26.85 (t); 26.85 (t); 26.08 (t); 5.63 (t); 24.41 (t);

MS: 252 (s); 224 (5); 195 (6); 164 (7); 150 (8); 135 (24); 123 (12); 107 (26); 96 (47); 82 (97); 67 (100); 55 (60); 41 (53); 29 (8); and a musk-like, odor similar to ambrette musk, Musk 174 and thibetolide.

Example 7

The procedure of Example 7 was performed analogously to the procedure of Example 3.

27.4 g of (3-carboxypropyl)triphenylphosphonium bromide (63.8 mmol) were placed in 100 ml of THF and treated with 17.2 g (153 mmol) of potassium t-butylate in 25 ml of THF. 28.5 g (60%, 69 mmol) of 11-bromoundecanal were added to this mixture. After the usual working up 20 g of crude product were obtained and after chromatography 14 g (66%) of 9Z-15-bromopentadec-4-enoic acid were obtained having the following characteristics: Z/E=91/9;

IR (liquid): 3008; 2926; 2854; 1711; 7436; 1281; 1252; 1211;

$^1$H-NMR (CDCl$_3$) 5.4 (2H) m; 3.4 (2H) t$\delta$=7 Hz; 2.4 (4H) m; and

MS 300 (2); 258 (9); 238 (35); 150 (17); 137 (25); 123 (32); 110 (38); 96 (88); 82 (91); 69 (98); 55 (100); 41 (86); 29 (32).

Example 8

17 g of potassium carbonate were placed under a nitrogen atmosphere and suspended in 200 ml of N-methylpyrrolidone. A solution of 13 g (41 mol) of Z-15-bromopentadec-4-enoic in 120 ml of N-methylpyrrolidone was added dropwise using a fine dosing dropping funnel during 7 hrs while stirring at 110–115° C. The mixture was stirred for 1 hour while cooling slowly. The reaction mixture was poured into water, extracted with ether, washed with water and saturated sodium chloride solution, dried over sodium sulphate and concentrated. The crude product (9.7 g) was chromatographed and distilled in a bulb-tube. 5.8 g (60%) of Z-oxacyclohexadec-5-en-2-one were obtained having the following characteristics: Z/E=91/9;

IR (film) 3008; 2928; 2857; 1737; 1459; 1350; 1254; 1166; 1041;

$^1$H-NMR (CDCl$_3$, 200 MHz) 5.41 (2H) m; 4.15 (2H) t $\delta$=6.2;

$^{13}$C-NMR (CDCl$_3$) 172.9 (s); 131.15 (d); 127.6 (d); 64.15 (t); 35.25 (t); 27.52 (t); 27.47 (t); 27.16 (t); 27.10 (t); 26.95 (t); 26.64 (t); 26.60 (t); 25.58 (t); 24.48 (t); 23.54 (t);

MS 238 (5); 220 (2); 178 (3); 163 (2); 149 (7); 135 (9); 126 (14); 112 (22); 96 (69); 82 (90); 67 (100); 55 (94); 41 (85); and a musk-like, fatty, powdery, lactone-like odor.

Example 9

The procedure of Example 9 was performed analogously to the procedure of Example 3.

48.5 g (0.1 mol) of (7-carboxyheptyl) triphenylphosphonium bromide were suspended in 150 ml of tetrahydrofuran. After the addition of 24.7 g (0.22 mol) of potassium t-butylate in 50 ml of tetrahydrofuran 26.4 g (0.12 mol) of 8-bromooctanal were added dropwise. After the usual work up 35.4 g of crude 8Z-16-bromohexadec-8-enoic acid were obtained having the following characteristics: Z/E=93/6;

IR: 3004; 2928; 2855; 1709; 1438; 1160; 1121; and $^1$H-NMR (CDCl$_3$) 5.35 (2H) m; 3.4 (2H) t $\delta$=6,25; 2.35 (2H) t $\delta$=7.5.

Example 10

The procedure of Example 10 was performed analogously to the procedure of Example 8.

41.5 g of potassium carbonate were placed in 400 ml of N-methylpyrrolidone and treated with a solution of 34 g (0.1 mol) of 8Z-16-bromohexadec-8-enoic acid in N-methylpyrrolidone. After the usual work up 8 g of crude product were obtained. After chromatography and bulb-tube distillation there were isolated 11.2 g (44%) of 2-oxacycloheptadec-9-en-2-one were isolated having the following characteristics: Z/E=93/6;

IR (film): 3003; 2929; 2856; 1735; 1461; 1346; 1247; 1182; 1076;

$^1$H-NMR (CDCl$_3$, 200 Mhz) 5.39 (2H) m; 4.12 (2H) t $\delta$=5.5 Hz; 2.33 (2H) t $\delta$=7.5;

$^{13}$C-NMR (CDCl$_3$) 173.8 (s) 130.0 (d); 129.8 (d); 64.0 (t); 34.6 (t); 29.1 (t); 28.7 (t); 28.3 (t); 28.0 (t); 27.95 (t); 27.86 (t); 27.83 (t); 26.3 (t); 26.1 (t); 25.9 (t); 24.9 (t); and an intensive musk-like, lactone-like, after nitromusk, ambrette musk and ambretone (limonene aldehyde), woody, animalic odor.

Example 11

The procedure of Example 11 was performed analogously to the procedure of Example 3.

97 g (0.2 mol) of (7-carboxyheptyl)-triphenylphosphonium bromide were dissolved in 500 ml of tetrahydrofuran. 45 g (0.4 mol) of potassium t-butylate (0.4 mol) in 200 ml of tetrahydrofuran were then added. Thereafter, 26 g (0.2 mol) of 7-hydroxyheptan-2-one were added. After the usual work up 49 g of crude product were obtained. After chromatographic purification 27.6 g (60%) of 14-hydroxy-9-methyltetradec-8-enoic acid were obtained having the following characteristics: Z/E=80/20; and $^1$H-NMR (CDCl$_3$ 200 MHz) 5.1 (1H) 6 $\delta$=6.5 Hz; 3.65 (2H) t $\delta$=6.25 Hz; 2.3(2H) t=7.5 Hz.

EXAMPLE 12

The procedure of Example 12 was performed analogously to the procedure of Example 4.

24.5 g (95.5 mol) of 14-hydroxy-9-methyltetradec-8-enoic acid, (Z/E=80/20) were placed in 50 ml of glycerol and treated with 0.54 g of potassium hydroxide (50 percent). The resulting water was distilled off. Thereupon, the distillation headpiece was removed and the special headpiece (see FIG. 1) was fitted and filled with glycerol. After the addition of 1 g of sodium methylate the mixture was heated to 152° C., 6 mbar. After 24 hours the addition of 1 g of MeONa was again effected. After 48 hours extraction of the content of the special headpiece yielded 19 g of crude product. By chromatography 19 g (82%) of 10-methyloxacyclopentadec-9-en-2-one were obtained having the following characteristics: Z/E=80/20;

IR: (film) 2930; 2857; 1735; 1459; 1382; 1251; 1161; 1085;

$^1$H-NMR (CDCl$_3$ 200 MHz) 5.03 (1H)m; 4.15 (2H) t $\delta$=5.6 Hz (Z isomer) 4.11 (2H) t $\delta$=6.5 (E isomer) 2.35 (2H) m;

MS 238 (3); 210 (2); 149 (3); 135 (3); 123 (13); 109 (26); 95 (53); 81 (88); 67 (89); 55 (90); 41 (100);

$^{13}$C-NMR (CDCl$_3$) 173.8 (s); 134.8 (s); 126.2 (d); 64.4 (t); 34.3 (t); 31.3 (t); 28.5 (t); 28.3 (t); 27.5 (t); 26.9 (t); 26.6 (t); 26.1 (t); 25.5 (t); 24.8 (t); Z isomer;

$^{13}$C-NMR (CDCl$_3$) 173.7 (s); 133.9 (s); 126.0 (d); 63.5 (t); 38.8 (t); 33.4 (t); 28.9 (t); 28.4 (t); 27.1 (t); 26.8 (t); 25.5 (t); 24.4 (t); 23.9 (t); E isomer; and a musk-like, powdery, slightly fruity, waxy odor.

Example 13

1.14 g of 10 percent palladium-on-carbon were added to 13.5 g (57 mol) of 10-methyloxacyclopentadec-9-en 2-one in 60 ml of ethanol and the mixture was subsequently hydrogenated under normal pressure for 6.5 hours. Then, it was suction filtered over Celite and the solution was concentrated, chromatographed and distilled in a bulb-tube. 8.4 g (62%) of 10-methyloxacyclopentadecan-2-one were obtained having the following characteristics:

IR (film) 2928; 2859; 1735; 1459; 1377; 1343; 1247; 1113; 1047;

$^1$H-NMR (CDCl$_3$ 200 MHz) 4.14 (2H) m; 2.35 (2H) m; 0.86 (3H) d δ=7 Hz;

MS 240 (0.8); 169 (4); 151 (10); 141 (11); 135 (7); 123 (8); 112 (19); 97 (69); 83 (31); 69 (54); 55 (100); 41 (81); 29 (33); and a musk-like, lactone-like, woody, nitromusk, powdery, earthy odor.

Example 14

The procedure of Example 14 was performed analogously to the procedure of Example 3.

45.7 g (0.1 mol) of (5-carboxypentyl)triphenylphosphonium bromide were placed in 200 ml of tetrahydrofuran and 25 g (0.22 ol) of potassium t-butylate in 100 l of tetrahydrofuran were added dropwise at 0° C. Then, 15.8 g (0.1 mol) of 9-hydroxy2-nonanone were added. After stirring for 30 minutes and usual work up, 28.5 g of crude 14-hydroxy-7-methyltetradec-6-enoic acid were obtained.

Example 15

138.5 g of crude 14-hydroxy-7-methyltetradec-6-enoic acid, prepared according to the preceding Example, were dissolved in 400 ml of methanol, treated with 3 ml of sulphuric acid and heated to reflux temperature for 1 hour. After usual work up and distillation 93 g (90%) of methyl 14-hydroxy-7-methyltetradec-6-enoate were obtained having the following characteristics, Z/E=60/40;

IR (film) 3380; 2930; 2856; 1742; 1437; 1173; 1059;

$^1$H-NMR (CDCl$_3$; 200 MHz) 5.1 (1H) t δ=7 Hz: 3.68 (3H) s; 3.65 (2H) t δ=6.25 Hz; 2.31 (2H) t δ=7.5; and MS: 270 (1); 220 (2); 171 (7,8); 138 (16); 123 (31); 109 (19); 95 (61); 81 (87); 67 (65); 55 (100); 41 (63); 29 (19).

Example 16

84.5 g (0.31 mol) of methyl 14-hydroxy-7-methyltetradec-6-enoate, 21 g of 86 percent potassium hydroxide in 220 ml of methanol, 72 g of chloropropane-1,2-diol and 9 ml of 5.4M methanolic sodium methylate solution were mixed according to the procedure in Example 6. The product was distilled (b.p. 114° C.) in a high vacuum (0.1 Torr) and subsequently chromatographed. 29 g (38%) of 8-methyloxacyclopentadec-7-en-2-one were obtained having the following characteristics, Z/E=60/40;

IR (film) 2931; 2858; 1736; 1459; 1234; 1153; 1058;

$^1$H-NMR (CDCl$_3$ 200 MHz) 5.06-5.22 (1H) m; 4.05-4.2 (2H) m; 2.22-2.4 (2H) m;

$^{13}$C-NMR (CDCl$_3$) 173.6 (s); 173.5 (s); 135.8 (s), 134.9 (s); 125.1 (d); 124.3 (d); 63.6 (t); 63.5 (t); 35.1 (t); 33.9 (t); 29.8 (t); 29.5 (t); 28.8 (t); 28.1 (t); 27.63 (t); 27.62 (t); 27.36 (t); 27.2 (t); 26.8 (t); 26.5 (t); 26.0 (t); 25.93 (t); 25.8 (t); 25.1 (t); 24.7 (t); 24.5 (t); 23.2 (9); 15.4 (9); and a weak after musk odor.

Example 17

25 g (0.10 mol) of Z-8-methyloxacyclopentadec-7-en-2-one were dissolved in 150 ml of methanol and hydrogenated (1.5 hours) with 2 g of 5% palladium-on-carbon with 100 mbar over-pressure. Then, the mixture was filtered over Celite, and the solution was concentrated, distilled in a bulb-tube and chromatographed. There were obtained 20 g (83%) of 8-methyloxacyclopentadecan-1-one were obtained having the following characteristics:

IR (CDCl$_3$) 2930; 2859; 1736; 1460;1246; 1167;

$^1$H-NMR (CDCl$_3$ 200 MHz) 4.3-4.0 (2H) m; 2.5-2.2 (2H) m; 0.85 (3H) d δ=7.0 Hz.;

$^{13}$C-NMR (CDCl$_3$) 173.9 (s); 63.8 (t); 34.9 (t); 33.9 (t); 32.2 (t); 30.5 (d); 28.4 (t); 28.2 (t); 26.9 (t); 26.2 (t); 24.8 (t); 24.8 (t); 24.5 (t); 23.3 (t); 20.8 (q). MS 240 (1); 138 (12); 125 (15); 110 (11); 97 (21); 83 (35); 69 (57); 55 (100); 41 (84); 27 (39); and a musk odor similar to ambrette musk and ambrettolide. as well as a powdery, flowery, nitromusk, amber-like, fruity odor.

Example 18

The procedure of Example 18 was performed analogously to the procedure of Example 3.

95 g (0.2 mol) of (6-carboxyhexyl)triphenylphosphonium bromide in 600 ml of tetrahydrofuran were added to 48 g (0.42 mol) of potassium t-butylate in 200 ml of tetrahydrofuran. Thereafter, 29 g (0.18 mol) of 8-hydroxy-6-methyl-2-octanone were added. After work up and chromatography 26 g (48%) of 14-hydroxy-8,12-dimethyltetradec-7-enoic acid were obtained having the following characteristics: Z/E=58/42;

IR (film) 2930; 2857; 1710; 1461; 1202; 1062;

$^1$H-NMR (CDCl$_3$; 200 MHz) 5.1 (1H) t δ=7.5; 3.7 (2H) m; 2.33 (2H) t δ=7 Hz; 0.9 (3H) d δ=6.3; and MS 270 (2); 252 (7); 137 (15); 123 (77); 109 (26); 95 (62); 81 (100); 69 (55); 55 (88); 41 (55); 29 (19).

Example 19

24.5 g (0.09 mol) of 14-hydroxy-8,12-dimethyltetradec-7-enoic acid were dissolved in 50 ml of methanol and treated and with phenolphthalein. 6 g of 85 percent potassium hydroxide were dissolved in 50 ml of methanol and titrated until a colour change took place. Subsequently, the methanol was distilled off and 80 ml of glycerol were added. 30 ml thereof were distilled off. Thereafter, 20 g (0.18 mol) of chloropropane-1,2-diol were added at 130° C. and the mixture was stirred at 130° C. for 1 hour. The excess chloropropane-1,2-diol was distilled off and treated at 70° C. with 4 ml of 5.4M methanolic sodium methylate solution. Heating to reflux temperature was carried out for 48 hours with the special headpiece (see Figure). The product-glycerol mixture was poured into 1 liter of water and extracted three times with hexane. The organic phase was washed with saturated potassium bicarbonate solution, dried, concentrated and distilled in a bulb-tube in a high vacuum. 19 g (83%) of 9, 13-dimethyloxacyclopent-8-en-2-one were obtained having the following characteristics: Z/E=58/42;

IR (film) 2928; 2858; 1734; 1457; 1378; 1249; 1152; 1068;

$^1$H-NMR (CDCl$_3$, 200 MHz) 5.1 (1H) m; 4.3-3.92 (2H) m; 2.31 (2H) t δ=6.5 Hz; 0.9 (3H) t δ=6 Hz;

$^{13}$C-NMR (CDCl$_3$) 174.1 (s); 174.0 (s); 134.9 (s); 134.2 (s); 125.7 (d); 125.6 (d); 62.5 (t); 62.1 (t); 38.5 (t); 37.0 (t); 35.9 (t); 34.38 (t); 34.35 (t); 34.2 (t); 33.6 (t); 30.1 (t); 29.8 (d); 29.4 (d); 28.8 (t); 28.5 (t); 27.9 (t); 27.3 (t); 27.2 (t); 26.9 (t); 25.2U (t); 24.8 (t); 24.5 (t); 23.1 (t); 22.9 (q); 19.5 (q); 18.6 (q); 15.2 (q);

MS 252 (11); 245 (45); 137 (15); 123 (93); 108 (29); 95 (60); 81 (100); 67 (53); 55 (79); 41 (59); 29 (23); and a musk-like, fruity, powdery, lactone-like, earthy, odor having good adhesion.

Example 20

9 g (0.035 mol) of 9,13-dimethyloxacyclopent-8-en-2-one were dissolved in 100 ml of ethyl acetate, 1 g of 5% palladium on active charcoal was added and the mixture was hydrogenated under normal pressure. Then, it was filtered over Celite, concentrated and distilled in a bulb-tube. 9 g (99%) of 9,13-dimethyloxa-cyclopentan-2-one were obtained having the following characteristics:

IR (film) 2928; 2859; 1736; 1459; 1378; 1245; 1156; 1116; 1056;

$^1$H-NMR (CDCl$_3$) 4.4-3.92 (2H) m; 2.5-2.2 (2H) m;

$^{13}$C-NMR 174.1 (s); 174.0 (s); 62.19 (t); 62.15 (t); 36.5 (t); 35.9 (t); 35.27 (t); 35.26 (t); 34.9 (t); 33.9 (t); 33.8 (t); 33.4 (t); 33.2 (t); 30.6 (d); 29.4 (d); 27.8 (t); 27.4 (d); 27.32 (d); 27.31 (t); 26.7 (t); 26.5 (t); 25.0 (t); 24.7 (t); 24.5 (t); 22.7 (t); 22.2 (t); 20.5 (q); 20.3 (q); 19.6 (q); 19.1 (q);

MS 245 (45); 170 (30); 152 (35); 140 (55); 125 (47); 111 (33); 97 (62); 83 (66); 69 (87); 55 (100); 41 (85); 29 (43); and a musk-like, fruity, powdery, flowery, lactonic, earthy, fatty odor

Example 21

The procedure of Example 21 was performed analogously to the procedure of Example 3.

60 g (0.13 mol) of (5-carboxypentyl)triphenylphosphonium bromide were suspended in 250 ml of tetrahydrofuran. 30 g (0.26 mol) of potassium t-butylate in 20 ml of tetrahydrofuran were then added. Subsequently, 26 g (0/11 mol) of 10-bromodecanal were added. After usual work up 28 g (65%) of crude 6Z-16-bromohexadec-6-enoic acid were obtained having the following characteristics: Z/E=93/7;

IR (film) 2927; 2854; 1709; 1438; 1162; 1121; 723;

$^1$H-NMR (CDCl$_3$ 200 MHz) 5.36 (2H) m; 3.4 (2H) t δ=6.3 Hz; 2.4 t δ=7.5 Hz; and MS 252 (15); 183 (9); 152 (14); 137 (11); 123 (15); 110 (17); 96 (39); 81 (51); 69 (66); 55 (100); 41 (70).

Example 22

The procedure of Example 22 was performed analogously to the procedure of Example 8.

25 g of potassium carbonate were suspended in 300 ml of N-methyl pyrrolidone. 30 g (0.09 mol) of crude 6Z-16-bromohexadec-6-enoic acid in 200 ml of N-methyl- pyrrolidone were added dropwise while stirring at 110–115° C. within 10 hours. After usual work up 18 g of crude product were obtained, and after chromatography 12 g (53%) of Z-oxacycloheptadec-7-en-2-one were obtained having the following characteristics: Z/E=93/7;

IR: (film) 3002; 2928; 2856; 1735; 1461; 1233; 1147;

$^1$H-NMR (CDCl$_3$ 200 MHz) 5.32 (2H) m; 4.12 (2H) t δ=5.5 Hz; 2.31 (2H) t δ=7.5 Hz;

$^{13}$C-NMR (CDCl$_3$) 173.4 (s); 130.3 (d); 129.4 (d); 64.4 (t); 34.8 (t); 29.0 (t); 28.5 (t); 28.2 (t); 27.9 (t); 27.6 (t); 27.3 (t); 27.2 (t); 26.8 (t); 26.0 (t); 25.8 (t); 24.7 (t);

MS 252 (2); 109 (11); 95 (29); 81 (53); 67 (69); 55 (74); 41 (100); 27 (53); and a ambrette seeds, fruity, musk-like, fatty, flowery odor.

Example 23

The procedure of Example 23 was performed analogously to the procedure of Example 3.

130 g (0.24 mol) of (11-carboxyundecyl)triphenylphosphonium bromide were placed in 800 ml of tetrahydrofuran. 58 g (0.51 mol) of potassium t-butylate in 200 ml of tetrahydrofuran were added and then 28 g (0.26 mol) of 4-chlorobutanyl were added. After usual work up 60 g (86%) of crude 12Z-16-chlorohexadec-12-enoic acid were obtained having the following characteristics: Z/E=97/3;

IR (film) 3005; 2926; 2854; 1709; 1438; 1285; 1167; 723; 694;

$^1$H-NMR (CDCl$_3$ 200 MHz) 5.5-5.2 (2H) m; 3.51 (2H) t δ=6.5; 2.32 (2H) t δ=7.5 Hz; and MS 252 (9); 123 (11); 109 (19); 95 (45); 81 (92); 68 (100); 55 (100); 41 (82); 29 (19).

Example 24

The procedure of Example 24 was performed analogously to the procedure of Example 8.

45 g of potassium carbonate were placed in 700 ml of N-methylpyrrolidone. A solution of 57.6 g (0.2 mol) of 16-chlorohexadec-12-enoic acid in 300 ml of N-methylpyrrolidone was added dropwise at 100–110° C. within 5 hours. After work up and chromatography 28 g (55%) of 13Z-oxacyclohept-13-en-2-one were obtained having the following characteristics: Z/E=97/3;

IR (film) 3004; 2928; 2856; 1737; 1459; 1343; 1248; 1169;

$^1$H-NMR 5.45-5.27 (2H) m; 4.12 (2H) t; 2.34 (3H) t;

$^{13}$C-NMR 173.7(s); 130.9 (d); 128.4(d); 63.6 (t); 34.1 (t); 28.8 (t); 27.8 (t); 27.5 (t); 27.5 (t); 27.2 (t); 27.1 (t); 26.8 (t); 26.7 (t); 26.1 (t); 24.6 (t); 23.8 (t);

MS: 252 (1); 109 (9); 95 (27); 81 (67); 67 (100); 55 (70); 41 (88); 27 (23); and a musk-like odor similar to musk ketone, as well as a powdery odor which is less fruity than ambrettolide and is similar to ambrette. In addition, the compound has a lactonic, fatty and flowery odor as well.

Example 25

The procedure of Example 25 was performed analogously to the procedure of Example 3.

164.6 g (0.37 mol) of (4-carboxybutyl)triphenylphosphonium bromide were suspended in 700 ml of tetrahydrofuran. 101 g (0.9 mol) of potassium t-butylate in 150 ml of tetrahydrofuran were added and then 68 g (0.36 mol) of 11-hydroxy-2-undecanone in 50 ml of tetrahydrofuran were added After usual working up there were obtained 98 g of crude 5Z-6-methylpentadec-5-enoic acid.

Example 26

98 g of crude 6-methylpentadec-5-enoic acid acid (from the proceeding Example) were dissolved in 305 ml of methanol, treated with 2 ml of sulphuric acid and heated to reflux temperature 2 hours. Then, the mixture was poured into water, made basic with saturated potassium bicarbonate solution, extracted twice with t-butyl methyl ether, concentrated and distilled in a high vacuum (0.1 Torr, 162–170° C.). 75 g (85%) of methyl 6-methylpentadec-5-enoate were obtained having the following characteristics: Z/E=56/46;

IR (film) 3365; 2928; 2855; 1741; 1437; 1369;

$^1$H-NMR (CDCl$_3$) 5.1 (1H) t δ=7.5 Hz; 3.65 (3H)s; 3.62 (2H) t δ=6.25 Hz; 2.3 (2H) t δ=7.5 Hz; and MS 284 (2); 201 (2); 173 (6); 151 (8); 137 (23); 124 (26); 109 (31); 95 (77); 82 (91); 67 (79); 55 (100); 41 (76); 27 (26).

Example 27

The procedure of Example 27 was performed analogously to the procedure of Example 6.

87 g (0.3 mol) of methyl 5Z-6-methylpentadec-5-enoate and 19.5 g of 86 percent potassium hydroxide were dissolved in 200 ml of methanol. 66 g of 3-chloropropane-1,2-diol and 200 ml of glycerol as well as, 5 ml of 5.4M methanolic sodium methylate solution were added. After usual work up the product were distilled in a high vacuum over a Vigreux column. 59 g (78%) of 7-methyloxacyclohexadec-6-en-2-one were obtained having the following characteristics: Z/E=56/46;

IR (film) 2928; 2856; 1737; 1456; 1309; 1241; 1153;

$^1$H-NMR (CDCl$_3$ 200 MHz) 5.1 (1H) m; 4.15 (2H) m; 2.32 (2H) m;

$^{13}$C-NMR 173.7(s); 173.5 (s); 136.0 (s); 135.5 (s); 124.4 (d); 124.2 (d); 64.8 (t); 64.0 (t); 38.9 (t); 34.3 (t); 32.5 (t); 30.4 (t); 28.2 (t); 27.67 (t); 27.66 (t); 27.34 (t); 27.31 (t); 27.29 (t); 27.23 (t); 26.84 (t); 26.79 (t); 26.72 (t); 26.69 (t); 26.2 (t); 25.9 (t); 25.8 (t); 25.7 (t); 25.5 (t); 24.3 (t); 22.8 (q); 14.9 (q);

MS 252 (13); 210 (12); 151 (13); 140 (15); 124 (22); 110 (33); 95 (100); 81 (90); 67 (66); 55 (85); 41 (68); 29 (21); and a musk-like, fruity, green odor.

Example 28

28 g (0.11 mol) of 7-methyloxacyclohexadec-6-en-2-one were dissolved in 200 ml of ethyl acetate and hydrogenated in the presence of 2 g of 5% palladium-on-carbon under 150 mbar of hydrogen. The mixture was filtered over Celite, concentrated and distilled in a bulb-tube. 26 g (92%) of 7-methyloxacyclohexadecan-2-one were obtained having the following characteristics:

IR (film) 2929; 2858; 2858; 1737; 1461; 1377; 1237; 1167; 1111;

$^1$H-NMR (CDCl$_3$ 200 MHz) 4.3-4.1 (2H) m; 2.33 (2H) m; 0.86 (3H) d δ=6.5 Hz;

$^{13}$C-NMR (CDCl$_3$) 173.8 (s); 63.7 (t); 35.39 (t); 34.49 (t); 33.31 (t); 30.49 (d); 28.23 (t); 27.07 (t); 26.77 (t); 26.16 (t); 26.06 (t); 26.01 (t); 25.38 (t); 25.02 (t); 24.07 (t); 20.57 (q);

MS 254 (0.4); 210 (4); 137 (6); 124 (41); 111 (32); 97 (42); 83 (67); 69 (72); 55 (100); 41 (63); 29 (17); and a musk-like, flowery, fruity, lactonic, powdery odor.

Example 29

The procedure of Example 29 was performed analogously to the procedure of Example 3.

100 g (0.2 mol) of (8-carboxyoctyl)triphenylphosphium bromide were placed in 500 ml of tetrahydrofuran and treated with 47 g (0.42 mol) of potassium t-butylate in 300 ml of tetrahydrofuran and then with 33 g (0.17 mol) of 7-bromoheptanal. After usual work up and chromatography 49 g (74%) of 9Z-16-bromo-hexadec-9-enoic acid were obtained having the following characteristics: Z/E=98/2;

IR (film) 3004; 2928; 2854; 1709; 1463; 1285; 937;

$^1$H-NMR (CDCl$_3$, 200 MHz) 5.35 (2H) m; 3.4 (2H) t δ=6.5 Hz; 2.35 (2H) t δ=7.5 Hz; and MS 232 (0.39); 316 (3); 272 (7.8); 252 (49); 234 (6); 182 (5); 164 (10); 150 (17); 137 (24); 123 (29); 110 (33); 96 (57); 83 (68); 69 (96); 55 (100); 41 (96); 29 (35).

Example 30

The procedure of Example 30 was performed analogously to the procedure of Example 8.

40 g (0.29 mol) of potassium carbonate were suspended in finely pulverized form in 600 mg of N-methylpyrrolidone. 49 g (0.147 mol) of Z-16-bromohexadec-9-enoic acid in 300 ml of N-methylpyrrolidone were added dropwise within 6 hours. A standard work up was effected; bulb-tube distillation and recrystallization gave 19 g (51%) of 10Z-oxacydoheptadec-10-en-2-one were obtained having the following characteristics: Z/E=98/2;

IR (film) 3002; 2929; 2856; 1736; 1460; 1343; 1242; 1177; 1059; 722;

$^1$H-NMR (CDCl$_3$, 200 MHz) 5.36 (2H) m; 4.15 (2H) t δ=5.5 Hz; 2.34 (2H) t δ=6.5 Hz;

$^{13}$C-NMR (CDCl$_3$) 173.61 (s); 130.12 (d); 129.88 (d); 64.11 (t); 34.51 (t); 29.05 (t); 28.46 (t); 28.32 (t); 27.98 (t); 27.68 (t); 27.57 (t); 26.31 (t); 25.77 (t); 25.64 (t); 25.00 (t);

MS 284 (2); 201 (2); 173 (6); 151 (8); 137 (23); 124 (26); 109 (31); 95 (77); 82 (91); 67 (79); 55 (100); 41 (76); 27 (26); and a musk-like odor similar to ambrette musk and an ambrettolide, powdery, strong, fruity, green, earthy, mossy odor.

Example 31

The procedure of Example 31 was performed analogously to the procedure of Example 3.

94 g (0.2 mol) of (6-carboxyhexyl)triphenylphosphonium bromide were suspended in 500 ml of tetrahydrofuran. 47 g (0.42 mol) of potassium t-butylate in 200 ml of tetrahydrofuran were added, followed by 50 g (0.22 mol) of 9-bromononanal. After work up and chromatography 52 g (78%) of 7Z-16-bromohexadec-7-enoic acid were obtained having the following characteristics: Z/E=90/10;

IR (film) 3004; 2927; 2854; 1709; 1462; 1277; 1239; 939;

H-NMR (CDCl$_3$, 200 MHz) 5.36 (2H) m; 3.4 (2H) t δ=7 Hz; 2.35 (2H) t δ=7.5 Hz; and MS 252 (13); 150 (7); 123 (13); 110 (18); 96 (36); 83 (43); 69 (60); 55 (100); 41 (67); 29 (20).

Example 32

The procedure of Example 32 was performed analogously to the procedure of Example 8.

41 g of potassium carbonate were suspended in 600 ml of N-methyl-pyrrolidone. A solution of 51 g (0.15 mol) of 7Z-16-bromohexadec-7-enoic acid in 400 ml of N-methylpyrrolidone was added dropwise at 90° C. within 8 hours. After usual work up and chromatography 30 g (77%) of 8Z-oxacycloheptadec-8-en-2-one were obtained having the following characteristics: Z/E=90/10;

IR (film) 3000; 2927; 2855; 1736; 1460; 1385; 1257; 1184; 1069;

$^1$H-NMR (CDCl$_3$, 200 MHz) 5.3 (2H) m; 4.13 (2H) t δ=6 Hz; 2.32 (2H) t δ=7 Hz;

$^{13}$C-NMR (CDCl$_3$) 173.71 (s); 130.04 (d); 129.88 (d); 63.51 (t); 34.37 (t); 29.29 (t); 28.66 (t); 28.58 (t); 28.38 (t); 28.32 (t); 28.22 (t); 27.51 (t); 26.81 (t); 26.66 (t); 25.19 (t); 25.13 (t);

MS 252 (4); 149 (8); 137 (8.6); 123 (13); 109 (23); 96 (62); 81 (100); 67 (97); 54 (64); and a musk-like, dry odor similar to ambrette seed oil, as well as a powdery, flowery, fruity, lactone-like, animalic odor.

Example 33

The procedure of Example 33 was performed analogously to the procedure of Example 3.

325 g (0.7 mol) of (5-carboxypentyl) triphenylphosphonium bromide were dissolved in 1500 ml of tetrahydrofuran. After the addition of 180 g (1.6 mol) of potassium t-butylate in 700 ml of tetrahydrofuran the mixture was treated with 175 g (0.71 mol) of 9-hydroxy-2-decanone (70% purity). After usual work up 186 g of crude 14-hydroxy-7-methyl-pentadec-6-enoic acid were obtained. This product was dissolved in 400 ml of methanol and, after the addition of 5 ml of concentrated sulphuric acid, heated to reflux for 2 hours. After work up, bulb-tube distillation and chromatography 102 g (50%) of methyl 14-hydroxy-7-methyl- pentadec-6-enoate were obtained having the following characteristics:

IR (film) 3419; 2929; 2856; 1741; 1437; 1374; 1201; 1172;

$^1$H-NMR (CDCl$_3$, 200 MHz) 5.1 (1H) t δ=7.5 Hz; 3.8 (2H) m; 3.68 (3H) s; 2.3 (2H) t δ=7.5 Hz; 1.19 (3H) d δ=6.3 Hz; and MS 284 (3); 266 (4); 168 (2); 149 (10); 137 (28); 123 (14); 108 (35); 95 (74); 81 (100); 67 (57); 55 (78); 41 (41); 29 (11).

Example 34

The procedure of Example 34 was performed analogously to the procedure of Example 19.

105 g (0.37 mol) of methyl 14-hydroxy-7-methylpentadec-6-enoate and 26 g (0.388 mol) of 86 percent potassium hydroxide were dissolved in 200 ml of methanol and treated with 90 g (0.8 mol) of 3-chloropropane-1,2-diol in 300 ml of glycerol as well as 15 ml of 30 percent methanolic potassium methylate solution. After the addition of the methylate solution the distillation headpiece was replaced by a special headpiece (see FIG. 1) and heated under reflux at 180° C. under 2–4 mbar for 4 hours. After extraction 69.5 g (74%) of 8,15-dimethyloxacyclopent-7-en-2-one were obtained having the following characteristics: Z/E=6/4;

IR (film) 2920; 2857; 1731; 1459; 1376; 1237; 1130; 1056;

$^1$H-NMR (CDCl$_3$, 200 MHz) 5.11 (1H) m; 4.94 (1H) m; 1.56 (3H) s; 1.21 (3H) d δ=6.25 Hz;

$^{13}$C-NMR (CDCl$_3$) 173.44 (s); 173.24 (s); 135.98 (s); 134.85 (s); 125.29 (d); 124.41 (d); 70.27 (d); 70.16 (d); 38.32 (t); 35.73 (t); 35.58 (t); 34.71 (t); 34.26 (t); 29.74 (t); 29.55 (t); 28.89 (t); 27.80 (t); 27.69 (t); 27.46 (t); 27.34 (t); 26.88 (t); 25.95 (t); 25.74 (t); 25.11 (t); 24.98 (t); 24.44 (t); 23.98 (t) 23.26 (q); 20.53 (q); 19.61 (q); 15.40 (q);

MS 252 (4); 154 (15); 137 (15); 121 (7); 107 (30); 95 (88); 81 (100); 67 (73); 55 (93); 41 (80); 29 (26); and a musk-like, powdery odor similar to nitromusk as well as an animalic, fatty odor.

Example 35

The procedure of Example 35 was performed analogously to the procured of Example 5.

422 g (0.8 mol) of 10-carboxydecyl-triphenylphosphonium bromide and 204 g (1.81 mol) of potassium t-butylate were reacted in 1.8 liters of THF and treated with 200 g (1.12 mol) of 70% 3-methyl-5-oxo-pentanol acetate from Example 2. Analogous work up as in Example 5 gave 297 g of crude product. This product was esterified analogously to Example 5 and, after working up and distillation, gave 168.9 g (70.9%) of 16-hydroxy-14-methyl-hexadec-11-en-oate were obtained having the following characteristics: (Z/E=95/5);

IR (liquid) 3419; 3005; 2926; 2854; 1741; 1458; 1436; 1375; 1265; 1197; 1172; 1058;

H-NMR (CDCl$_3$) 5.4 (2H) m; 3.7 (3H) s; 2.3 (2H) t ;1.9 (2H) d; and

MS 298 (0.39); 185 (7); 109 (22); 95 (33); 81 (100); 74 (18); 68 (31); 55 (57); 41 (30); 29 (9).

Example 36

The procedure of Example 36 was performed analogously to the procedure of Example 6.

42 g (0.14 mmol) of methyl 16-hydroxy-14-methyl-hexadec-11-enoate were reacted with 9 g of potassium hydroxide in 100 ml of methanol, treated with 150 ml of glycerol and the methanol and 50 ml of glycerol were distilled off. Then, the mixture was reacted with 30 g of 3-chloropropane-1,2-diol at 150° C. for 1 hour and evaporated to 70 ml under 3 mm vacuum. After the addition of 3 ml of 30% potassium methylate solution in methanol the mixture was refluxed for 58 hours at 170–190° C. (3–4 mbar) as in Example 6 using the special headpiece. After working up as described in Example 6 35:8 of crude product were obtained. After distillation 26.3 g (70%) of 15-methyl-oxacycloheptadec-12-en-2-one were obtained having the following characteristics: Z/E=95/5;

IR (film) 3006; 2927; 2855; 1736; 1460; 1347; 1250; 1174; 1150; 1118; 1052;

H-NMR (CDCl$_3$) 5.4 (2H) m; 4.18 (1H) m; 4.10 (1H) m; 2.3 (2H) t; 0.96 (3H) d;

13C-NMR (CDCl$_3$) 173.7 (s); 131 (d); 127.7 (d); 62.4 (t); 35.1 (t); 34.6 (t); 34.2 (t); 30.6 (d); 28.4 (t); 28.1 (t); 27.9 (t); 27.4 (t); 27.21 (t); 27.15 (t); 26.0 (t); 24.4 (t); 19.2 (q);

MS 266 (4 ); 251 (2); 238 (5); 224 (10); 123 (7); 109 (19); 95 (30); 81 (100); 68 (47); 55 (53); 41 (43); 29 (15); and a musk, woody, animalic, sweet, earth, fruity, homogeneous odor.

Example 37

The procedure of Example 37 was performed analogously to the procedure of Example 3.

68.1 g (149 mmol) of (4-carboxy-3-methyl-butyl)-triphenylphosphonium bromide were placed in 150 ml of THF and treated with 33.4 g (298 mmol) of potassium t-butylate in 50 ml of THF. 35 g (149 mmol) of 10-bromodecanal were added to this mixture After usual work up 111.8 g of crude product were obtained and, after chromatography, 29 g of 3-methyl-5Z-15-bromopentadec-5-enoic acid were obtained having the following characteristics:

IR (film) 3005; 2926; 2853; 1707; 1309;

H-NMR (CDCl$_3$) 1 (3H) d; 3.4 (2H) m; 5.4 (2H) m; and

MS 272 (31); 252 (14); 230 (4); 192 (6); 151 (10); 123 (12); 110 (18); 95 (43); 81 (67); 68 (100); 55 (70); 41 (50); 29 (15).

Example 38

The procedure of Example 38 was performed analogously to the procedure of Example 8.

17.4 g of potassium carbonate were placed in 320 ml of N-methylpyirolidone and treated dropwise with a solution of 28 g (84 mmol) of 3-methyl-5Z-15- bromopentadec-5-enoic acid in 240 ml of N-methylpyrrolidone. After usual work up 21.2 g of crude product was obtained After chromatography and bulb-tube distillation 15.4 g of Z-4-methyloxacyclohexadec-6-en-2-one were obtained having the following characteristics:

IR (film) 3006; 2927; 2855; 1735; 1458; 1379; 1305; 1252; 1172; 1147; 1079;

H-NMR (CDCl$_3$) 1 (3H) d; 4.01 (1H) m; 4.3 (1H) m; 5.4 (2H) m;

MS 252 (4); 210 (4); 192 (5); 149 (4); 135 (8); 121 (12); 110 (25); 95 (43); 81 (78); 67 (78); 55 (78); 41 (100); 27 (33); and a musk, fruity, woody, earthy, mossy odor.

Example 39

0.5 g of 10 percent palladium-on-charcoal was added to 5.1 g (20 mmol) of Z4-methyloxacyclohexadec-6-en-2-one in 20 ml of ethanol and the mixture was subsequently hydrogenated under normal pressure for 2 hours. Then, the mixture was suction filtered over Celite and the solution was concentrated, chromatographed and distilled in a bulb-tube. 4 g (78%) of 4-methyloxacyclohexadecan-2-one. were obtained having the following characteristics:

IR (film) 2928; 2857; 1735; 1460; 1380; 1252; 1174; 1113;

H-NMR (CDCl$_3$) 0.95 (3H) d; 2.22 (2H) d; 4.03 (1H) m; 4.21 (1H) m;

13 CNMR (CDCl$_3$) 173.3 (s); 63.8 (t); 42 (t); 35 (t); 30 (d); 28.2 (t); 26.8 (t); 26.6 (t); 26.3 (t); 26.2 (t); 25.6 (t); 25.5 (t); 25.0 (t); 24.8 (t); 20.1 (q);

MS 254 (0.7); 194 (10); 166 (4); 152 (4); 138 (6); 124 (9); 110 (15); 96 (32); 87 (35); 82 (44); 69 (66); 55 (100); 41 (86); 29 (30); and a musk, fresh, animalic, powdery, woody odor similar to pine needles.

Example 40

Odorant compositions a) Accord: Fresh, flowery, rose, violets, suitable e.g. for feminine eau de Cologne.

|  | Parts by Weight |
|---|---|
| Compound of Example 4 | 10 |
| BENZYL ACETATE EXTRA | 40 |
| 3-CIS-HEXENYL ACETATE | 1 |
| PHENYLETHYL ALCOHOL | 80 |
| α-HEXYLCINNAMALDEHYDE | 100 |
| BERGAMOT RECONSTITUTION | 150 |
| BERRYFLOR | 30 |
| CITRONELLOL EXTRA | 40 |
| CYCLAL C | 2 |
| β-DAMASCONE 10% DPG | 2 |
| DIPROPYLENE GLYCOL | 90 |
| EBANOL | 5 |
| ETHYLLINALOOL | 100 |
| FLORHYDRAL | 6 |
| CITRONELLYL FORMATE | 7 |
| GARDENOL | 4 |
| GIVESCONE | 8 |
| HEDIONE | 50 |
| HYDROXYCITRONELLAL | 30 |
| INDOLENE 10% DPG | 5 |
| ISORALDEINE 95 | 80 |
| CIS-JASMONE | 2 |
| KEPHALIS | 50 |
| LILIAL | 50 |
| ROSE OXIDE | 1 |
| HEXYL SALICYLATE | 5 |
| TANGERINE OIL | 2 |
| TERPINEOL PURE | 30 |
| TROPIONAL | 20 |
|  | 1000 |

In this composition the compound of Example 4 confers volume and musk Odor, rounds off the flowery notes and gives the accord more cosmetic character.

b) Accord: Flowery, green, spicy, suitable e.g. for shampoos, soaps and toilet articles.

|  | Parts by weight |
|---|---|
| Compound of Example 4 | 15 |
| BENZYL ACETATE EXTRA | 60 |
| DIMETHYLBENZYLCARBINOL ACETATE | 30 |
| GERANYL ACETATE | 40 |
| PHENYLETHYL ALCOHOL | 120 |
| α-HEXYLCINNAMALDEHYDE | 120 |
| 10-UNDECEN-1-AL | 5 |
| PHENYLACETALDEHYDE 85% IN PHENYLETHYL ALCOHOL | 2 |
| BERGAMOT GIVCO 104 | 140 |
| CEDARWOOD OIL VIRGIN. | 10 |
| CYCLOHEXAL | 40 |
| GERANIOL PURE | 50 |
| CLOVE BUD ESS. | 5 |
| HEDIONE | 40 |
| HELIOTROPIN | 10 |
| ISOEUGENOL | 2 |
| ISORALDEINE 95 | 50 |
| LILIAL | 50 |
| LINALOOL SYNT. | 60 |
| MANDARIN OIL COMMON | 20 |
| PECHE PURE | 1 |
| BENZYL SALICYLATE | 80 |
| 3-CIS-HEXENYL SALICYLATE | 10 |
| TROPIONAL | 10 |
| VERTOFIX COEUR | 30 |
|  | 1000 |

The compound of Example 4 confers volume to the composition by its musk and lactone-like character, rounds off the green notes and combines the spicy notes with the flowery notes. Moreover, the compound of Example 4 enhances the substantivity of the composition.

c) Fresh, flowery bouquet, e.g. for cosmetics and for soaps.

|  | Parts by weight |
| --- | --- |
| Compound of Example 8 | 20 |
| BENZYL ACETATE EXTRA | 30 |
| L-BORNYL ACETATE PURE | 6 |
| LINALYL ACETATE SYNTH. | 80 |
| p-TERT. BUTYLCYCLOHEXYL ACETATE | 100 |
| VERDYL ACETATE | 15 |
| α-HEXYLCINNAMALDEHYDE | 130 |
| ALLYL AMYL GLYCOLATE | 3 |
| CEDARWOOD OIL VIRGIN. | 10 |
| DAMASCENONE 10% DPG | 5 |
| DIHYDROMYRCENOL | 80 |
| DIMETHYLOCTENONE | 7 |
| DIPROPYLENE GLYCOL | 30 |
| GIVESCONE | 10 |
| HEDIONE | 40 |
| INDOLENE | 4 |
| ISORALDEINE 95 | 100 |
| LEMAROME N | 5 |
| LINALOOL SYNT. | 200 |
| NECTARYL | 10 |
| OKOUMAL | 10 |
| TANGERINE OIL | 1 |
| VERTOFIX COEUR | 100 |
|  | 1000 |

This fresh, flowery bouquet for cosmetics and soaps becomes richer by the addition of the compound of Example 8, and has the desired musk note and volume, and confers a cosmetic effect to the composition.

d) Flowery-oriental, feminine accord, e.g. for cosmetics, e.g. Colognes.

|  | Parts by weight |
| --- | --- |
| Compound of Example 28 | 20 |
| BENZYL ACETATE EXTRA | 30 |
| CITRONELLYL ACETATE | 6 |
| LINALYL ACETATE SYNTH. | 50 |
| PHENYLETHYL ALCOHOL | 50 |
| α-AMYLCINNAMALDEHYDE | 150 |
| 10-UNDECEN-1-AL 10% DPG | 3 |
| ALLYL AMYL GLYCOLATE | 4 |
| BERGAMOT GIVCO 104 | 80 |
| CARBITOL | 30 |
| CARDAMONE ESS. CEYLON | 2 |
| CASSIONE (FIRMENICH) 10% DPG | 5 |
| COUMARIN PURE CRYST. | 5 |
| CYCLAL C 10% DPG | 5 |
| DIPROPYLENE GLYCOL | 100 |
| EBANOL | 10 |
| ETHYL LINALOOL | 80 |
| GERANIOL EXTRA | 20 |
| GERANIOL PURE | 8 |
| HEDIONE | 100 |
| INDOLE 10% DPG | 3 |
| ISO E SUPER | 50 |
| CIS-JASMONE 10% DPG | 6 |
| MANDARIN OIL ESS-RECONSTITUTION | 50 |
| PATCHOULI OIL IRON-FREE | 20 |
| BENZYL SALICYLATE | 60 |

-continued

|  | Parts by weight |
| --- | --- |
| 3-CIS-HEXENYL SALICYLATE | 30 |
| STEMON | 3 |
| VANILLIN | 20 |
|  | 1000 |

This flowery-oriental, feminine accord becomes richer by the addition of the compound of Example 28. With its mild, musk-like character the compound gives to the composition more volume and velvety character which comes into play especially in cosmetics and Cologne.

e) Flowery accord, e.g. for cosmetics and shampoos.

|  | Parts by weight |
| --- | --- |
| Compound of Example 8 or 24 | 30 |
| BENZYL ACETATE EXTRA | 100 |
| DIMETHYLBENZYLCARBINOL ACETATE | 30 |
| GERANYL ACETATE | 30 |
| 3-CIS-HEXENYL ACETATE | 2 |
| LINALYL ACETATE | 50 |
| p-TERT BUTYLCYCLOHEXYL ACETATE | 80 |
| VERDYL ACETATE | 0 |
| PHENYLETHYL ALCOHOL | 00 |
| ENDEC-10-EN-1-AL |  |
| 2-METHYL-UNDECANAL |  |
| BERRYFLOR | 0 |
| CITRONELLOL EXTRA | 60 |
| CYCLAL C | 3 |
| CYCLOHEXYLALLYL PROPIONATE | 15 |
| γ-DECALACTONE | 2 |
| DIHYDROMYRCENOL | 40 |
| DIPROPYLENE GLYCOL | 20 |
| EUGENOL PURE | 20 |
| FLORHYDRAL (3-(3-ISOPROPYLPHENYL)BUTANOL) | 10 |
| FRUCTONE (2-METHYL-1,3-DIOXOLAN-2-ACETIC ACID ETHYL ESTER) | 5 |
| GARDENOL | 20 |
| GERANONITRILE | 5 |
| HELIOTROPIN CRYST. | 20 |
| β-IONONE | 30 |
| JASMONYL | 50 |
| LILIAL | 80 |
| LINALOOL | 50 |
| ROSE OXIDE | 2 |
| TERPINEOL | 40 |
|  | 1000 |

This flowery bouquet becomes richer by the addition of the compounds of Example 24 or Example 8. The composition takes on a soft musk effect and has more volume.

f) Flowery lime blossom accord, e.g. for detergents.

|  | Parts by weight |
| --- | --- |
| Compound of Example 24 or 28 | 10 |
| CITRONELLYL ACETATE | 50 |
| VERDYL ACETATE | 100 |
| PHENYLETHYL ALCOHOL | 60 |
| HEXYLCINNAMALDEHYDE | 150 |
| 4-METHOXY BENZALDEHYDE | 25 |
| METHYL BENZOATE | 5 |
| COUMARIN | 15 |
| DIHYDROMYRCENOL | 60 |
| DIPROPYLENE GLYCOL | 30 |

-continued

| | Parts by weight |
|---|---|
| 3-CIS-HEXENOL | 10 |
| ISO E SUPER | 90 |
| ISORALDEINE 70 | 140 |
| LILIAL | 130 |
| NECTARYL | 20 |
| OKOUMAL | 15 |
| UNDECAVERTOL (4-METHYL-DEC-3-EN-5-OL) | 40 |
| VERDANTIOL (LILIAL METHYL ANTHRANILATE) | 50 |
| | 1000 |

The compound of Example 28 or Example 24 gives to this typical flowery lime blossom accord soft, musk-like volume and more substantivity; in particular, the soft musk-like note comes into play on damp and dry washing.

g) Flowery, fruity accord, e.g. for cosmetics, e.g. Colognes.

| | Parts by weight |
|---|---|
| Compound of Example 6 | 10 |
| BENZYL ACETATE EXTRA | 80 |
| VETIVENYL ACETATE | 40 |
| PHENYLETHYL ALCOHOL | 150 |
| α-HEXYLCINNAMALDEHYDE | 120 |
| DECANAL | 2 |
| 10-UNDECEN-1-AL | 1 |
| METHYL ANTHRANILATE EXTRA | 1 |
| BERGAMOT GIVCO 104 | 120 |
| DIPROPYLENE GLYCOL | 30 |
| ETHYL LINALOOL | 100 |
| EUGENOL PURE | 20 |
| GARDENOL | 5 |
| INDOLENE | 3 |
| ISOEUGENOL | 3 |
| ISORALDEINE 70 | 60 |
| METHYL CEDRYL KETONE | 80 |
| NECTARYL | 5 |
| NONADYL | 30 |
| BENZYL SALICYLATE | 100 |
| 30CIS-HEXENYL SALICYLATE | 20 |
| SANDALORE | 20 |
| | 1000 |

In this flowery, fruity, feminine accord with woody undertones the compound of Example 6 with its musk-like character accompanies the flowery notes and confers more strength to the fruity elements. This accord is especially suitable for Colognes and cosmetics.

h) Fresh, spicy, woody accord, e.g. for cosmetics, e.g. Colognes for men

| | Parts by weight |
|---|---|
| Compound of Example 6 | 10 |
| BENZYL ACETATE EXTRA | 30 |
| GERANYL ACETATE PURE | 50 |
| ALLYL AMYL GLYCOLATE | 3 |
| METHYL ANTHRANILATE EXTRA | 1 |
| BASIL ESSENCE | 10 |
| BERGAMOT RGV 2 | 200 |
| CARBITOL | 60 |
| α-ISOMETHYLIONONE (α-KETONE) | 50 |
| LEMON OIL ARGENTINIAN | 100 |
| COUMARIN | 20 |

-continued

| | Parts by weight |
|---|---|
| DIHYDROMYRCENOL | 100 |
| TARRAGON OIL | 5 |
| EVERNYL | 3 |
| CLOVE BUD OIL | 15 |
| HEDIONE | 50 |
| ISO E SUPER | 50 |
| ISOEUGENOL | 3 |
| NUTMEG ESSENCE | 20 |
| PATCHOULI OIL | 30 |
| PETITGRAIN OIL PARAGUAY | 7 |
| SANDALORE | 20 |
| VANILLIN | 2 |
| | 1000 |

The compound of Example 6 confers to this fruity, spicy, woody accord more volume and a velvety, musk-like impression and rounds off the composition.

While the invention has been illustrated and described with respective illustrative embodiments and modes of practice, it will be apparent to those skilled in the art that various modifications and improvements may be made without departing from the scope and spirit of the invention. Accordingly, the invention is not to be limited by the illustrative embodiment and modes of practice.

We claim:

1. An odorant composition, which contains at least one 15–17 membered lactone compound of the formula

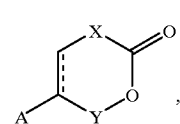

I wherein the dotted line signifies an optional additional bond but which in case of a 16-membered lactone compound is not placed at position 11, 12 or 13; one or both of X and Y is methylene or $C_{2-12}$-polymethylene, optionally substituted with an additional methyl group with the poviso that the sum of carbon atoms of X and Y is 11, 12 or 13, and A is hydrogen or methyl when the compound is unsaturated and methyl when the compound is saturated providing that the unsaturated compounds are in at least 80% of cis form when A is hydrogen and are in at least 50% of cis form when A is methyl, with the exception of Z-oxacyclopentadec-6-en-2-one, Z-oxacycloheptadec-8-en-2-one and Z-oxacycloheptadec-11-en-2-one.

2. An odorant composition according to claim 1, containing at least one compound selected from the group consisting of Z-oxacycloheptadec-12-en-2-one, Z-oxacylohexadec-5-en-2-one, Z-oxacycloheptadec-7-en-2-one, Z-oxacyclohetadec-13-en-2-one Z-oxacycloheptadec-10-en-2-one, Z-oxacvcloheqtadec-8-en-2-one, and Z-4-methyl-oxacyclohexadec-6-en-2-one.

3. An odorant composition according to claim 1 containing at least one compound selected from the group consisting of oxacycloheptadec-12-en-2-one, oxacycloheptadec-9-en-2-one, oxacycloheptadec-7-en-2-one, oxacycloheptadec-13-en-2-one, oxacycloheptadec-10-en-2-one, oxacycloheotadec-14-en-2-one, 15-methyl-oxacycloheptadec-12-en-2-one, 13-methyl-oxacyclopentadec-10-en-2-one, oxacyclohexadec-5-en-2-one, 10-methyl-oxacyclopentadec-9-en-2-one, 10-methyl-oxacyclopentadecan-2-one, 8-methyl-oxacyclopentadec-7- en-2-one, 8-methyl-oxacyclogentadecan-2-one, 9,13-dimethyl-oxacyclopentadec-8-en-2-one, 7-methyl-oxacyclohexadec-6-en-2-one, 4-methyl-oxacyclohexadecan-2-one, 7-methyl-oxacyclohexadecan-2-one, and 8,15-dimethyl-oxacyclopentadec-7-en-2-one.

4. An odorant composition according to claim 3, containing 13-methyl-oxacyclopentadec-10-en-2-one.

5. An odorant composition according to claim 4, wherein the 13-methyl-oxacyclopentadec-10-en-2-one has the Z-(13S)-configuration.

6. An odorant composition according to claim 4 wherein the 13-methyl-oxacyclopentadec-10-en-2-one has the Z-(13R)-configuration.

7. Compounds of the formula

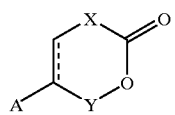

I' wherein the dotted line signifies an optional additional bond but which in case of a 16-membered lactone compound is not placed at position 11, 12 or 13, one or both of X and Y is methylene or $C_{2-12}$-polymethylene, optionally substituted with an additional methyl group with the proviso that the sum of carbon atoms of X and Y is 11, 12 or 13, and A is hydrogen or methyl when the compound is unsaturated and methyl when the compound is saturated providing that the unsaturated compounds are in at least 80% of cis form when A is hydrogen and are in at least 50% of cis form when A is methyl, with the exception of Z-oxacyclopentadec-3-en-2-one, Z-oxacyclopentadec-6-en-2-one, Z-oxacyclopentadec-13-en-2-one, Z-oxacyclohexadec-3-en-2-one, Z-oxacyclohexadec-6-en-2-one, Z-oxacycloheptadec-8-en2-one, Z-oxacycloheptadec-10-en-2-one, Z-oxacycloheptadec-11-en-2-one, Z-oxacycloheptadec-12-en-2-one, Z-oxacycloheptadec-13-en-2-one, and Z-oxacyclheptadec-15-en-2-one.

8. A compound according to claim 7 selected from the group consisting of Z-oxacylohexadec-5-en-2-one, Z-oxzcycloheptadec-7-en-2-one, and Z-4-methyloxacyclohexadecan-2-one.

9. A compound according to claim 7 having the formula 13-methyl-oxacyclopentadec-10-en-2-one.

10. A compound according to claim 7 having the formula Z-(13R)methyl-oxacyclopentadec-10-en-2-one.

11. A compound according to claim 9 having the formula Z-(13S)-methyl-oxacyloentadec-10-en-2-one.

12. A compound according to claim 7 selected from the group consisting of oxacyclohexadec-5-en-2-one, 10-methyl-oxacyclopentadec-9-en-2-one, 10-methyl-oxacyclopentadecan-2-one, 8-methyl-oxacyclopentadec-7-en-2-one, 8methyl-oxacyclopentadecan-2-one, 15-methyl-oxacycloheptadec-12-en-2-one, 9,13-dimethyl-oxacyclopentadec-8-en-2-one, 7-methyl-oxacyclohexadec-6-en-2-one, 7-methyl-oxacyclohexadecan-2-one, 4-methyl-oxacyclohexadecan-2-one, 8,15-dimethyl-oxacyclopentadec-7-en-2-one.

13. A process for the manufacture of the compounds of formula I according to claim 1, which process comprises lactonizing a compound of the formula

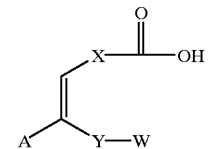

II wherein A is hydrogen or methyl when the compound is unsaturated and methyl when the compound is saturated providing that the unsaturated compounds are in at least 80% cis form when A is hydrogen and are in at least 50% cis form when A is methyl with the exception of Z-oxacyclopentadec-6-en-2-one, Z-oxacycloheptadec-8-en-2-one and Z-oxacycloheptadec-11-en-2-one; X and Y is methylene or $C_{2-12}$-polymethylene, optionally X and Y substituted with an additional methyl group; and W is OH, O-alkanoyl or a leaving group.

14. A process according to claim 13 wherein the leaving group is selected from the group consisting of mesylate, tosylate and halogens.

15. A process according to claim 13 wherein lactonization is performed at temperatures at least 80° C.

16. A process according to claim 15 wherein lactonization is performed at basic conditions.

17. A process according to claim 13 wherein a resulting unsaturated product of formula I is saturated using hydrogenation.

18. A process according to claim 16, wherein a compound of formula II in which W is a leaving group, the base used to lactonize the compound is potassium carbonate or sodium carbonate and N-methylpyrrolidone is the solvent.

19. A process according to claim 39, wherein a compound of formula II is prepared by subjecting a compound of the formula

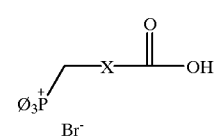

III to a Wittig reaction with a compound of the formula

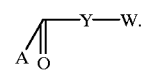

IV

20. A method for odorizing comprising administering a compound of formula I according to claim 7 or of a mixture thereof.

* * * * *

UNITED STATES PATENT AND TRADEMARK OFFICE
CERTIFICATE OF CORRECTION

PATENT NO.    : 6,255,276 B1
DATED         : July 3, 2001
INVENTOR(S)   : Georg Frater et al.

It is certified that error appears in the above-identified patent and that said Letters Patent is hereby corrected as shown below:

Column 26,
Line 42, please change "poviso" to -- proviso --.
Line 56, please change "oxacvclohegtadec" to -- oxacycloheptadec --.

Column 27,
Line 1, please change "oxacyclogentadecan" to -- oxacyclopentadecan --.
Line 38, please change "oxacyclheptadec" to -- oxacycloheptadec --.
Line 48, please change "oxacyloentadec" to -- oxacyclopentadec --.

Signed and Sealed this

Sixteenth Day of April, 2002

Attest:

JAMES E. ROGAN
*Director of the United States Patent and Trademark Office*

*Attesting Officer*